(12) United States Patent
Ohta et al.

(10) Patent No.: US 7,909,510 B2
(45) Date of Patent: Mar. 22, 2011

(54) RADIATION PHOTOGRAPHING APPARATUS

(75) Inventors: Yasunori Ohta, Kanagawa (JP);
Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 12/481,581

(22) Filed: Jun. 10, 2009

(65) Prior Publication Data

US 2009/0323900 A1     Dec. 31, 2009

(30) Foreign Application Priority Data

Jun. 26, 2008 (JP) .................................. 2008-166881

(51) Int. Cl.
*G03B 42/02* (2006.01)
(52) U.S. Cl. ...................................................... 378/167
(58) Field of Classification Search .................... 378/19, 378/98.8, 167–189
See application file for complete search history.

(56) References Cited

U.S. PATENT DOCUMENTS 7,210,847 B2 * 5/2007 Hack .............................. 378/189
7,569,831 B2 * 8/2009 Jadrich et al. ............. 250/370.11

FOREIGN PATENT DOCUMENTS

JP          10-177224        6/1998

* cited by examiner

*Primary Examiner* — Irakli Kiknadze
(74) *Attorney, Agent, or Firm* — Solaris Intellectual Property Group, PLLC

(57) ABSTRACT

A radiation photographing apparatus includes: a housing in which an opening portion for allowing ventilation of the inside of the housing with ambient air is formed at a side surface of the housing; a covering member provided at the side surface of the housing, that is made of an elastic material which absorbs impact acting from the outside of the housing, and covers the opening portion; and an opening and closing mechanism that opens and closes the covering member with respect to the opening portion is provided so deterioration of constituent components caused by external impact and heat is suppressed with a small number of components.

20 Claims, 17 Drawing Sheets

RADIATION PHOTOGRAPHING APPARATUS

CROSS-REFERENCE TO RELATED APPLICATION

This application claims priority under 35 USC 119 from Japanese Patent Application No. 2008-166881 filed on Jun. 26, 2008, the disclosure of which is incorporated by reference herein.

BACKGROUND OF THE INVENTION

1. Field of the Invention

The present invention relates to a radiation photographing apparatus which photographs a radiological image.

2. Related Art

As a radiation photographing apparatus (a radiographic apparatus), an X-ray photographing apparatus disclosed in Japanese Patent Application Laid-Open No. 10-177224 (Patent Document 1) is known. In the X-ray apparatus described in Patent Document 1, a ventilation hole to circulate air is formed in a lower portion of a frame, and a shutter to open and close the ventilation hole is arranged inside the ventilation hole.

A ventilation hole which circulates air is also formed in an upper portion of the frame, and a fan to circulate air is arranged inside the ventilation hole. Inside the fan, a shutter to open and close the ventilation hole is arranged.

According to this configuration, the fan exhausts air the temperature of which is increased by heat from a semiconductor element outside the apparatus, so that the semiconductor element or the like may be suppressed from increasing in temperature.

Deterioration of the constituent components such as a semiconductor element may be caused by not only heat but also external impact.

SUMMARY OF THE INVENTION

The present invention, in consideration of the above circumstances, provides a radiation photographing apparatus which can suppress a constituent component from being deteriorated by external impact and heat with a small number of components.

A radiation photographing apparatus according to a first aspect of the invention includes: a housing in which an opening portion for allowing ventilation of the inside of the housing with ambient air (for example, for admitting ambient air into the housing) is formed at a side surface of the housing; a covering member provided at the side surface of the housing, that is made of an elastic material which absorbs an impact from outside the housing, and covers the opening portion; and an opening and closing mechanism that opens and closes the covering member with respect to the opening portion.

According to this configuration, when the covering member which covers the opening portion is opened by the opening and closing mechanism, ambient air is taken into the housing through the opening portion. In this manner, a constituent component in the housing is cooled.

The covering member is made of an elastic material which absorbs impact acting from the outside of the housing. In this manner, since the covering member has the function of opening and closing the opening portion and the function of absorbing impact acting from the outside of the housing, in comparison with a configuration in which the functions are independently given by different members, the number of components can be suppressed from increasing.

As described above, according to the configuration of the first aspect, a constituent component can be suppressed from being deteriorated by external impact and heat with a small number of components.

In a radiation photographing apparatus according to a second aspect of the invention, in the configuration of the first aspect, opening portions are formed in a plurality of side surfaces of the housing respectively, and opening and closing mechanisms are provided at the respective side surfaces, and independently open and close the covering member at the respective side surfaces.

According to this configuration, only a portion of the covering member which is located at a location (side surface) which must be opened can be opened and the constituent component in the housing can be cooled without loss.

In a radiation photographing apparatus according to a third aspect of the invention, in the configuration of the first aspect, the opening and closing mechanism includes: a slider that is arranged to be slidably movable on the housing; and a link member whose distal end portion is rotatably attached to the covering member and whose proximal end portion is rotatably attached to the slider, and that opens the covering member by the distal end portion pushing the covering member toward the outside of the housing due to the slider moving to a facing position that faces a position of the covering member at which the distal end portion is attached.

In a radiation photographing apparatus according to a fourth aspect of the invention, in the configuration of the first aspect, the opening and closing mechanism includes an extendable rod that opens the covering member by extending to push the covering member.

In a radiation photographing apparatus according to a fifth aspect of the invention, in the configuration of the first aspect, the opening and closing mechanism includes: a biasing member that is biased toward a pushing position where the biasing member opens the covering member by pushing the covering member; and an engaging member that is engaged with the biasing member, and that is deformed at a predetermined temperature so as to release an engaging state with the biasing member to allow the biasing member to move to the pushing position.

In a radiation photographing apparatus according to a sixth aspect of the invention, in the configuration of the fourth aspect, the opening and closing mechanism is provided at a corner portion of the housing.

In a radiation photographing apparatus according to a seventh aspect of the invention, in the configuration of the fourth aspect, the opening and closing mechanism is provided at the side surface.

In a radiation photographing apparatus according to an eighth aspect of the invention, in the configuration of the fifth aspect, the engaging member is made of bimetal that extends at the predetermined temperature.

A radiation photographing apparatus according to a ninth aspect of the invention includes: a housing in which an opening for allowing ventilation of the inside of the housing with ambient air (for example, for admitting ambient air into the housing) is formed at a side surface of the housing; a covering member provided at the side surface of the housing, that is made of an elastic material which absorbs an impact from outside the housing, and covers the opening portion; and an opening and closing mechanism that opens and closes the covering member with respect to the opening portion, wherein the opening and closing mechanism opens the covering member with respect to the opening portion by pushing to elastically deform the covering member toward the outside of the housing.

In a radiation photographing apparatus according to a tenth aspect of the invention, in the configuration of the first aspect, a plurality of opening portions are formed in the side surface of the housing.

In a radiation photographing apparatus according to an eleventh aspect of the invention, in the configuration of the first aspect, the opening and closing mechanism includes: a cam member that is arranged to be rotatable on the housing; and a rotating driving section, connected to the cam member, that rotates the cam member, wherein the cam member includes a far portion which is located at the farthest position from a rotation axis of the cam member and a near portion which is located at the nearest position from the rotation axis, and when the cam member is rotated by the rotating driving section, and the far portion moves to a position where the far portion faces a portion of the covering member, the covering member opens the opening portion by the far portion pushing the covering member toward the outside the housing, and when the cam member is rotated by the rotating driving section, and the near portion moves to a position where the near portion faces the portion of the covering member, the covering member closes the opening portion.

The invention has the above configuration, thus the constituent component can be suppressed from being deteriorated by external impact and heat with a small number of components.

BRIEF DESCRIPTION OF THE DRAWINGS

Exemplary embodiments of the present invention will be described in detail with reference to the following figures, wherein.

DETAILED DESCRIPTION OF THE INVENTION

An example of an exemplary embodiment according to the present invention will be described below with reference to the accompanying drawings.

(Configuration of Electronic Cassette According to Exemplary Embodiment)

Figure 1:
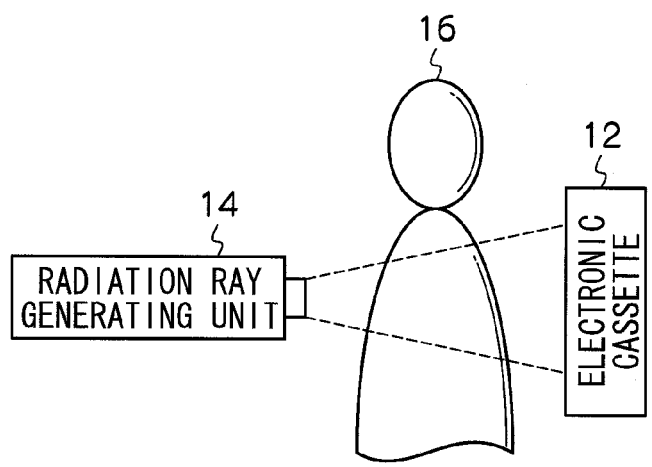
FIG. 1 is a schematic view showing an arrangement of an electronic cassette in a radiographic state.
Figure 2:
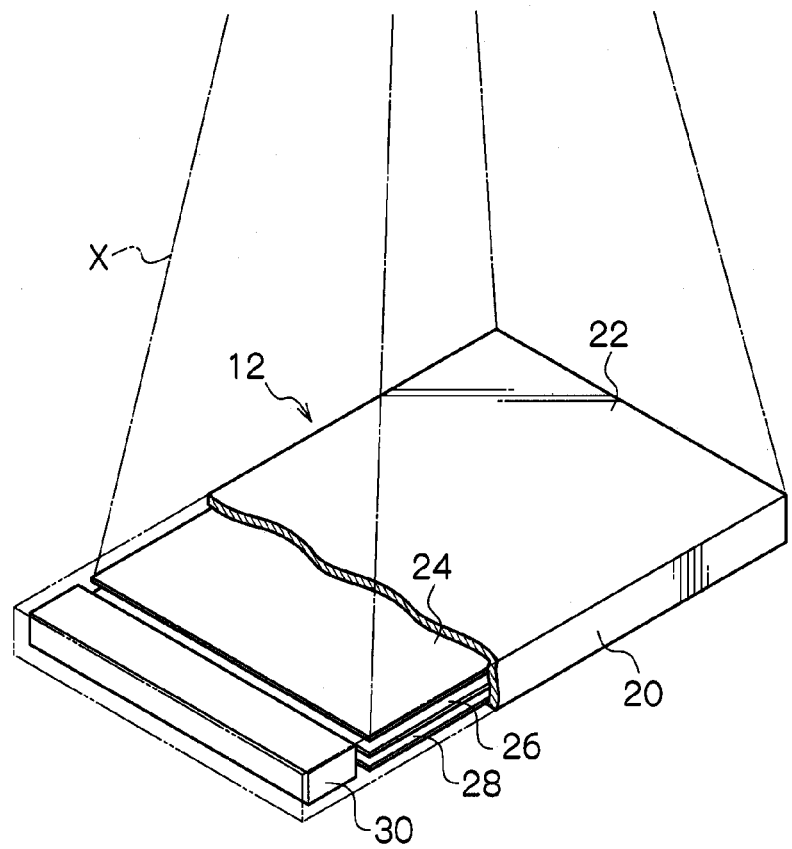
FIG. 2 is a schematic perspective view showing an internal structure of the electronic cassette.
Figure 3:
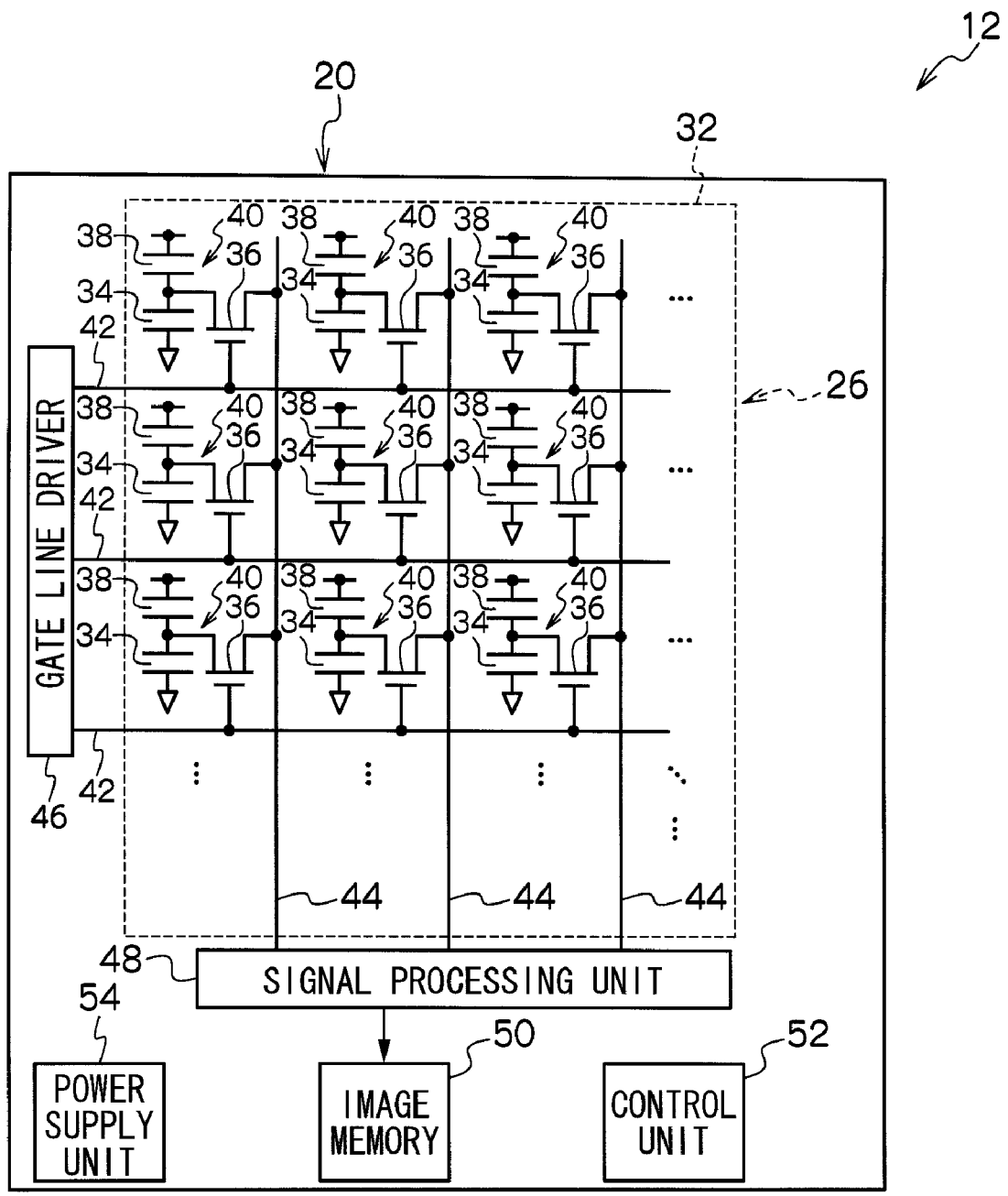
FIG. 3 is a block diagram showing a schematic configuration of the electronic cassette.

A configuration of an electronic cassette according to an exemplary embodiment will be described. FIG. 1 is a schematic view showing an arrangement of an electronic cassette at a time of radiation image photographing (at a radiographic state). FIG. 2 is a schematic perspective view showing an internal structure of the electronic cassette. FIG. 3 is a block diagram showing a schematic configuration of an electronic cassette 12.

An electronic cassette 12 according to the exemplary embodiment has portability, detects a radiation ray generated from a radiation source and transmitted through a photographic subject, generates image information of a radiological image (a radiation image) represented by the detected radiation ray, and can store the generated image information. More specifically, the electronic cassette 12 has the following configuration.

As the radiation photographing apparatus, not only the electronic cassette 12, but also, for example, a radiation photographing apparatus which has no portability or a radiation photographing apparatus which does not store the generated image information may be used.

As shown in FIG. 1, the electronic cassette 12, in photographing of a radiological image, is arranged to be spaced apart from a radiation ray generating unit 14 serving as a radiation source which generates radiation ray. A space between the radiation ray generating unit 14 and the electronic cassette 12 serves as a photographing position at which a photographic subject 16 is to be located. When the radiological image is designated to be photographed, the radiation ray generating unit 14 emits a radiation ray of a radiation dose according to a photographic condition or the like given in advance. The radiation ray emitted from the radiation ray generating unit 14 is transmitted through the photographic subject 16 located at the photographing position, so that the radiation ray holds the image information and then is irradiated on the electronic cassette 12.

As shown in FIG. 2, the electronic cassette 12 is made of a material which transmits a radiation ray X, and is provided with a planar housing 20 having a predetermined thickness. In the housing 20, sequentially from a side of an irradiation surface 22 on which the radiation ray X is irradiated in the housing 20, a grid 24 which removes scattered radiation of the radiation ray X generated when the radiation ray X is transmitted through the photographic subject 16, a radiation ray detector (radiation ray detection panel) 26, serving as an example of a radiation ray converter, which detects the radiation ray generated from the radiation ray generating unit 14 and transmitted through the photographic subject 16 and converts the radiation ray into radiological image information, and a lead plate 28 which absorbs back scattered radiation of the radiation ray X are housed. On a one-end side in the housing 20, a housing 30 which houses constituent components (see FIG. 3) such as a signal processing unit 48, a power supply unit 54, a control unit 52, and an image memory 50 is arranged.

The radiation ray detector 26 of the electronic cassette 12 is configured by stacking a photoelectric converting layer which absorbs a radiation ray to convert the radiation ray into electric charges on an TFT active matrix substrate 32 shown in FIG. 3. The photoelectric converting layer is made of amorphous a-Se (amorphous selenium) containing, for example, selenium as a main component (for example, a content rate of 50% or more). A radiation ray is irradiated on the photoelectric converting layer to generate inside electric charges (electron-hole pairs) of a quantity according to the radiation dose of the irradiated radiation ray, so that the irradiated radiation ray is converted into electric charges.

On the TFT active matrix substrate 32, a large number of pixel portions 40 (FIG. 3 schematically shows a photoelectric converting layer corresponding to each of the pixel portions 40 as a photoelectric converting unit 38) each having a storage (accumulation) capacitor 34 which accumulates electric charges generated by the photoelectric converting layer and a TFT 36 to read the electric charges accumulated in the storage capacitor 34 are arranged in the form of a matrix. Electric charges generated by the photoelectric converting layer with irradiation of radiation ray on the electronic cassette 12 are accumulated in the storage capacitor 34 of each of the pixel portions 40. In this manner, a radiological image represented by a radiation ray transmitted through the photographic subject and irradiated on the electronic cassette 12 is converted into image information obtained by the electric charges and held in the radiation ray detector 26.

On the TFT active matrix substrate 32, plural gate lines 42 extending in a predetermined direction (a row direction) to turn on/off the TFTs 36 of the respective pixel portions 40 and plural data lines 44 extending in a direction (a column direction) orthogonal to the gate lines 42 to read accumulated electric charges from the storage capacitors 34 through the ON TFTs 36 are arranged. Each of the gate lines 42 is connected to a gate line driver 46, and each of the data lines 44 is connected to a signal processing unit 48. When electric charges are accumulated in the storage capacitors 34 of the respective pixel portions 40, the TFTs 36 of the respective pixel portions 40 are sequentially turned ON in units of rows by signals supplied from the gate line driver 46 through the gate lines 42. The electric charges accumulated in the storage capacitors 34 of the pixel portions 40 the TFTs 36 of which are turned ON are transmitted through the data lines 44 as electric charge signals and input to the signal processing unit 48. Therefore, the electric charge accumulated in the storage capacitor 34 of the pixel portions 40 are sequentially read in units of rows.

The signal processing unit 48 includes an amplifier and a sample holding circuit which are arranged for each of the data lines 44, and an electric charge signal transmitted through each of the data lines 44 is amplified by the amplifier and then held in the sample holding circuit. To an output side of the sample holding circuit, a multiplexer and an A/D converter serving as an example of an electric signal converting unit which converts an electric signal having image information are sequentially connected. The electric charge signals held in the sample holding circuits are sequentially (serially) input to the multiplexer, and analog electric signals are converted into digital electric signals by the A/D converter. The image memory 50 is connected to the signal processing unit 48, and pieces of image information output from the A/D converter of the signal processing unit 48 are sequentially stored in the image memory 50. The image memory 50 has a storage capacitor which may store the pieces of image information of plural frames. Each time a radiological image is photographed, pieces of image information obtained by photographing are sequentially stored in the image memory 50.

The electronic cassette 12 includes the control unit 52 which controls an operation of an entire apparatus. The control unit 52 is configured by a microcomputer or the like which includes a CPU which controls the entire electronic cassette 12, a ROM serving as a storage medium in which various processing programs are stored, a RAM which temporarily stores data as a work area, and a memory serving as a storage unit in which various pieces of information are stored.

As the control unit, not only a control unit which controls an operation of the entire apparatus, but also a control unit which controls some operation of the apparatus may be used.

The electronic cassette 12 includes the power supply unit 54 which supplies an electric power to the constituent components of the various circuits and the various elements to operate the electronic cassette 12.

As the power supply unit 54, in order to prevent the portability of the electronic cassette 12 from being deteriorated, a configuration which builds a battery (rechargeable secondary battery) therein and supplies an electric power from the charged battery to the various circuits and the various elements is preferably used. However, a primary battery may be used as the battery, or a configuration which is always connected to a commercial power supply and rectifies and transforms an electric power supplied from the commercial power supply to supply the electric power to the various circuits and the various elements may be used.

As the power supply unit, not only a power supply unit which supplies an electric power to the constituent components of the entire apparatus, but also a power supply unit which supplies an electric power to some constituent components of the apparatus may be used. The electronic cassette 12 may be a configuration having plural power supply units.

(Configuration to Cool Heat Generating Portion of Electronic Cassette 12)

Figure 4:
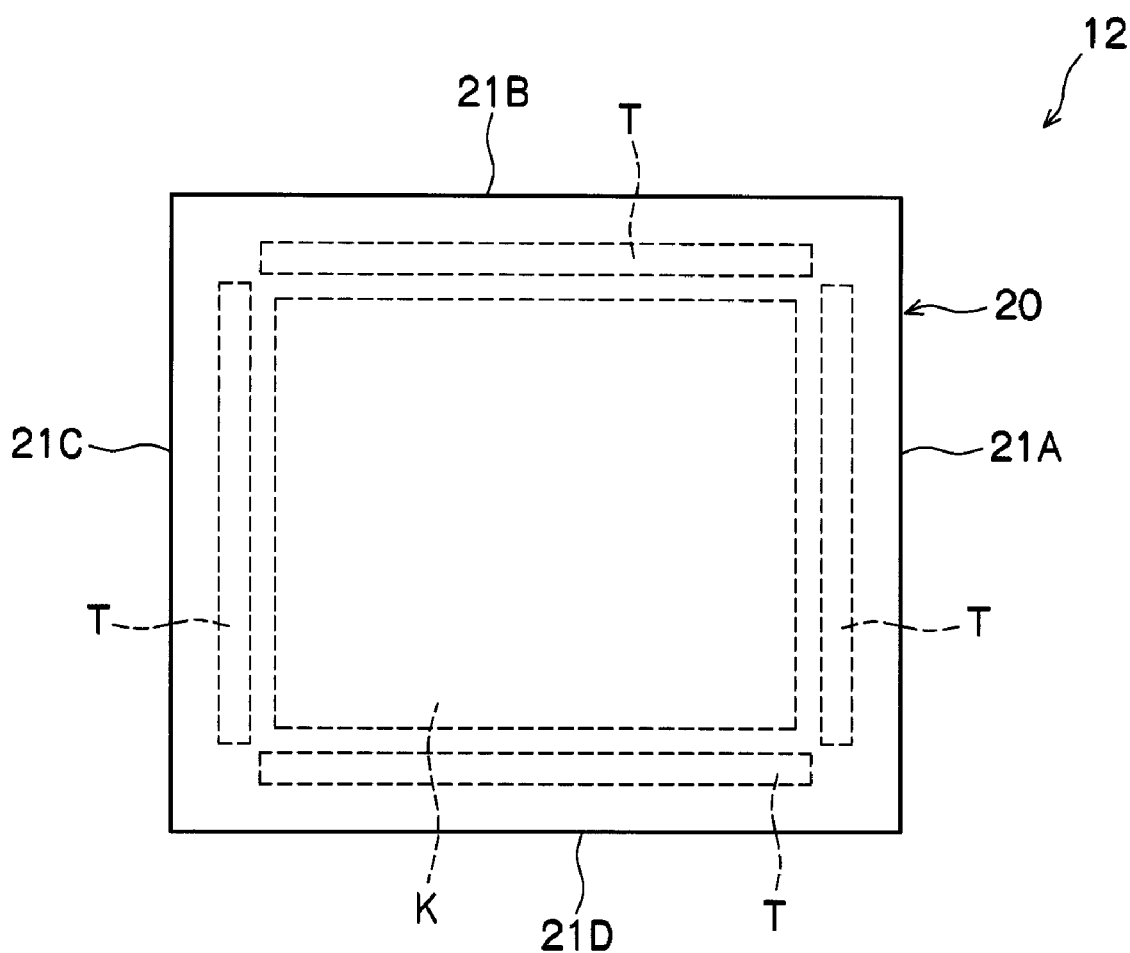
FIG. 4 is a schematic front view of the electronic cassette to show an arrangement position of a heat generating portion.
Figure 5:
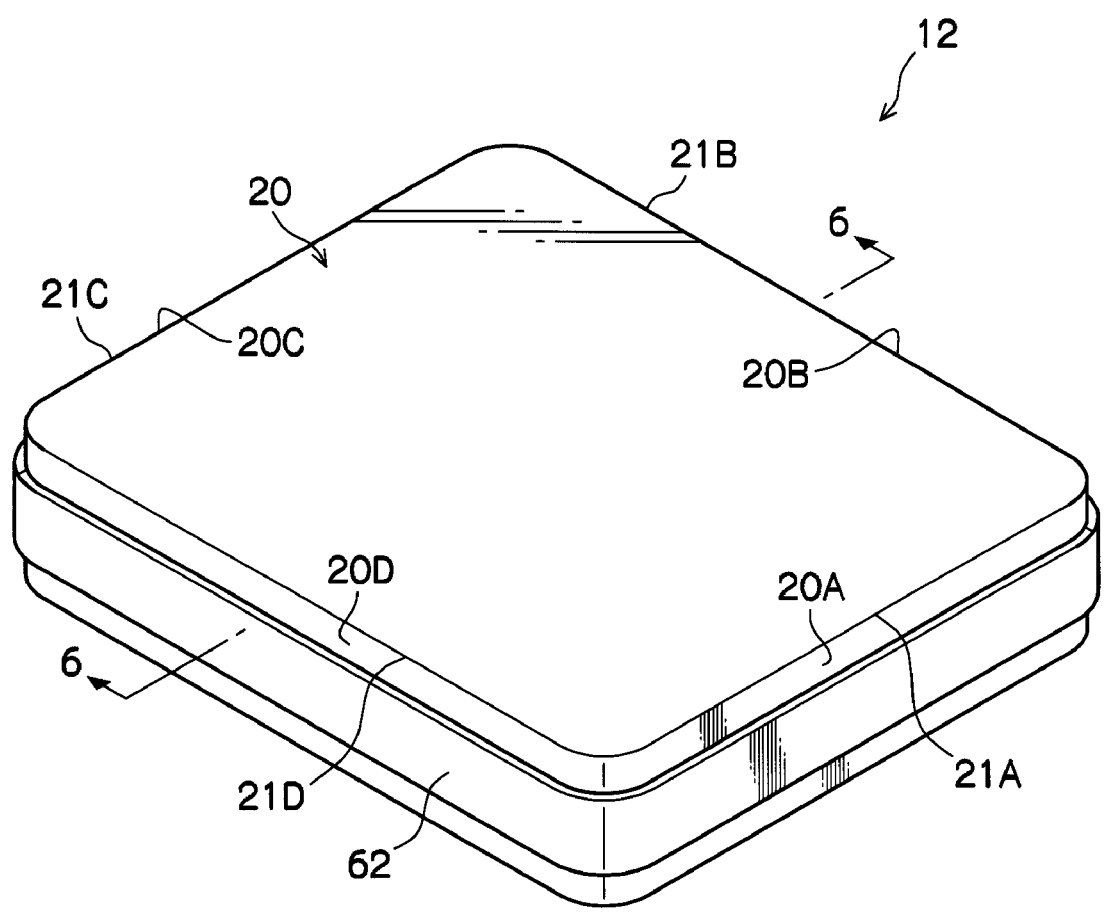
FIG. 5 is a perspective view showing an appearance of an electronic cassette according to the exemplary embodiment.
Figure 6:
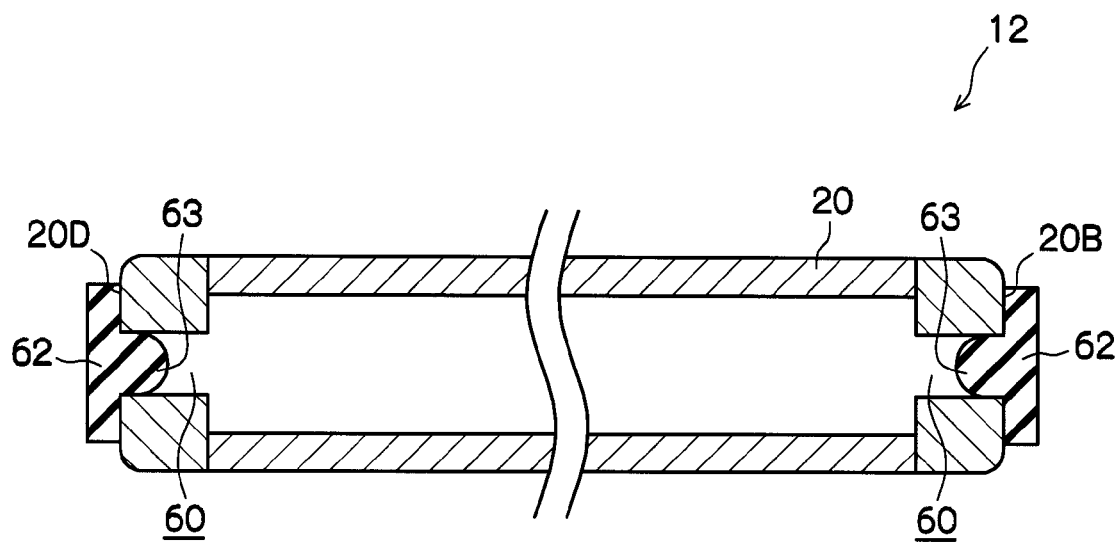
FIG. 6 is a sectional view along a 6-6 line in FIG. 5.

A configuration to cool a heat generating portion of the electronic cassette 12 will be described below. FIG. 4 is a schematic front view of the electronic cassette to show an arrangement position of the heat generating portions. FIG. 5 is a perspective view showing an appearance of an electronic cassette according to the exemplary embodiment. FIG. 6 is a sectional view along a 6-6 line in FIG. 5.

Figure 7:
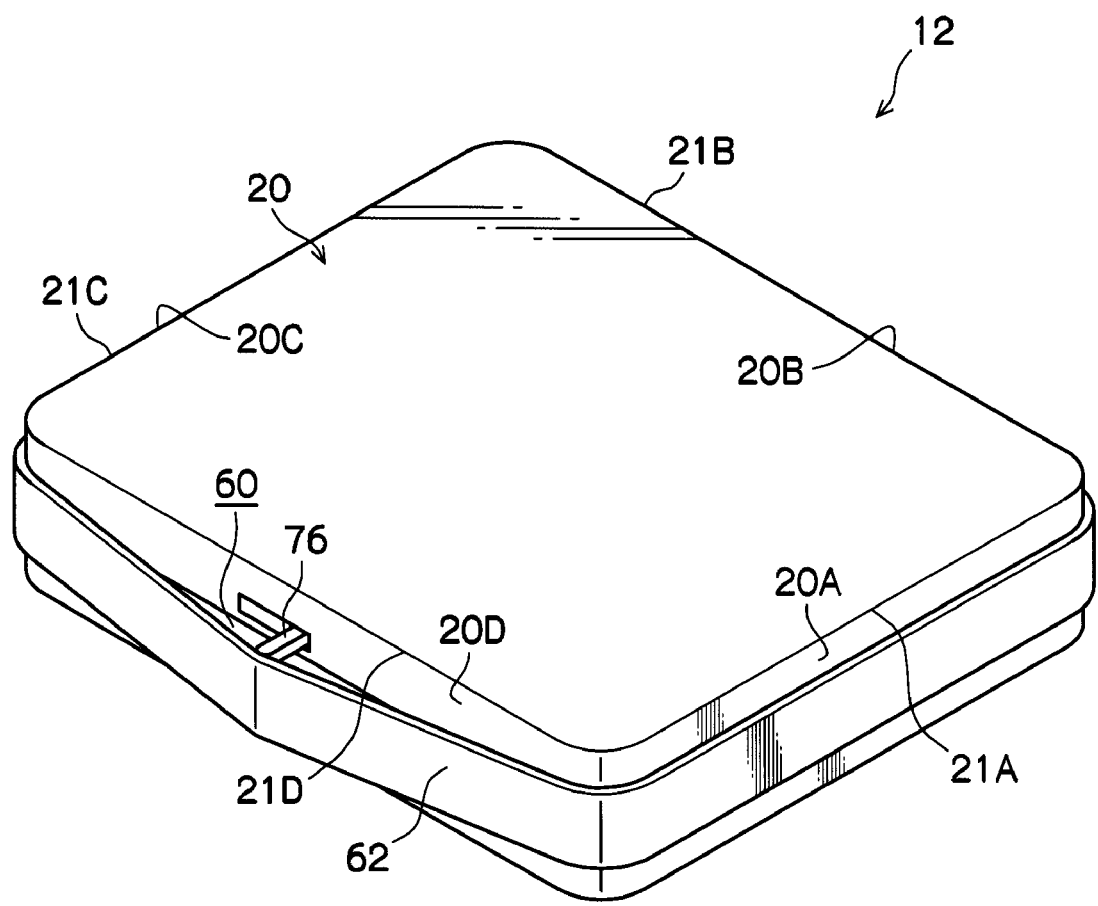
FIG. 7 is a perspective view showing an appearance of the electronic cassette according to the exemplary embodiment and showing a state in which an opening is opened.
Figure 8:
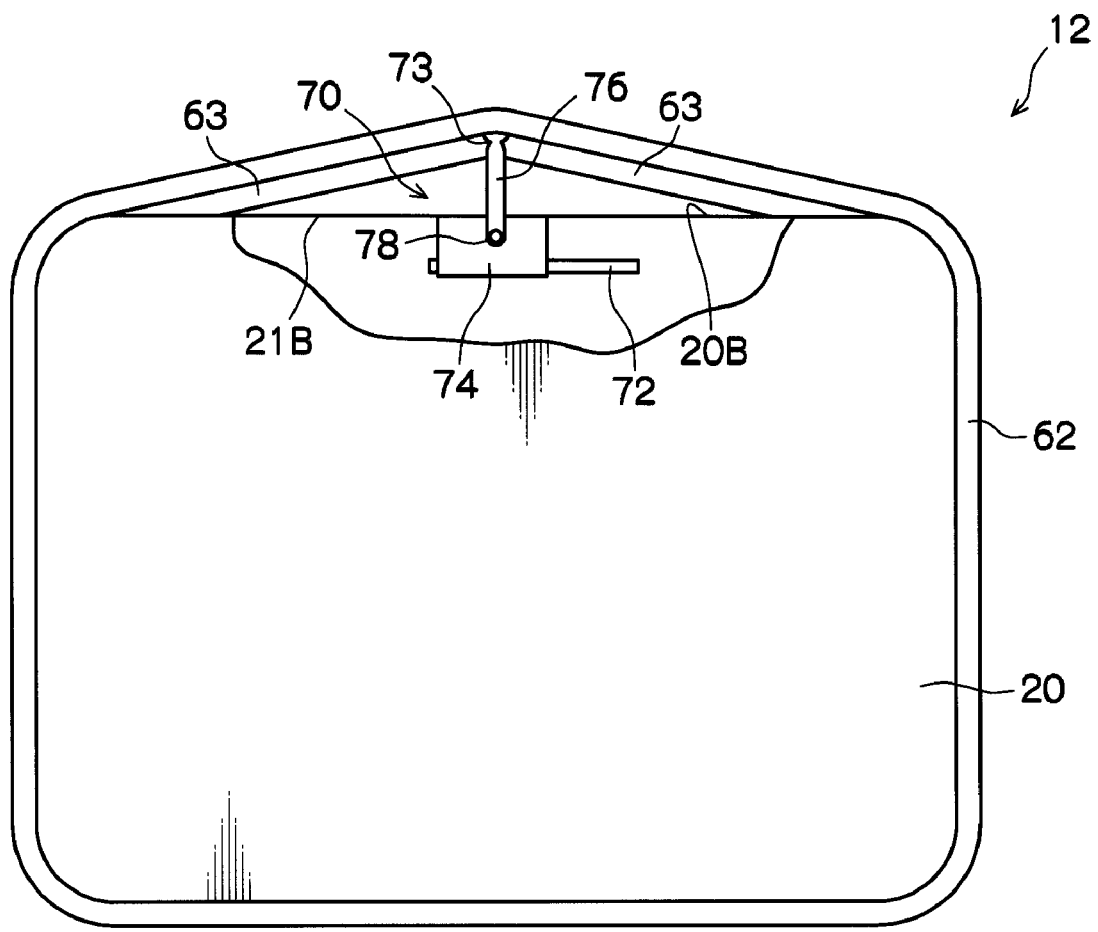
FIG. 8 is a schematic front view showing an opening and closing mechanism according to the exemplary embodiment and showing a state in which the opening is opened.

FIG. 7 is a perspective view showing an appearance of the electronic cassette according to the exemplary embodiment and showing a state in which an opening is opened. FIG. 8 is a schematic front view showing an opening and closing mechanism according to the exemplary embodiment and showing a state in which the opening is opened.

Figure 9:
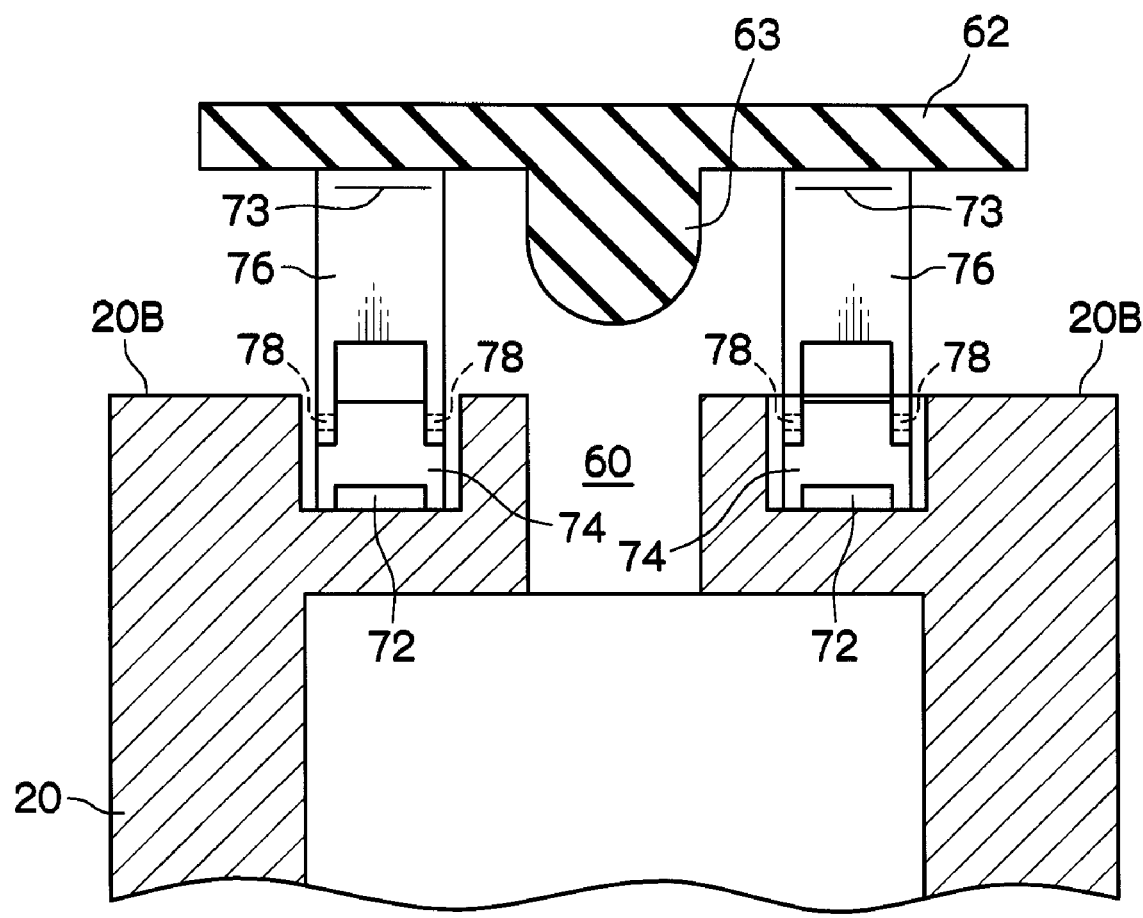
FIG. 9 is a partial sectional view showing the opening and closing mechanism according to the exemplary embodiment.
Figure 10:
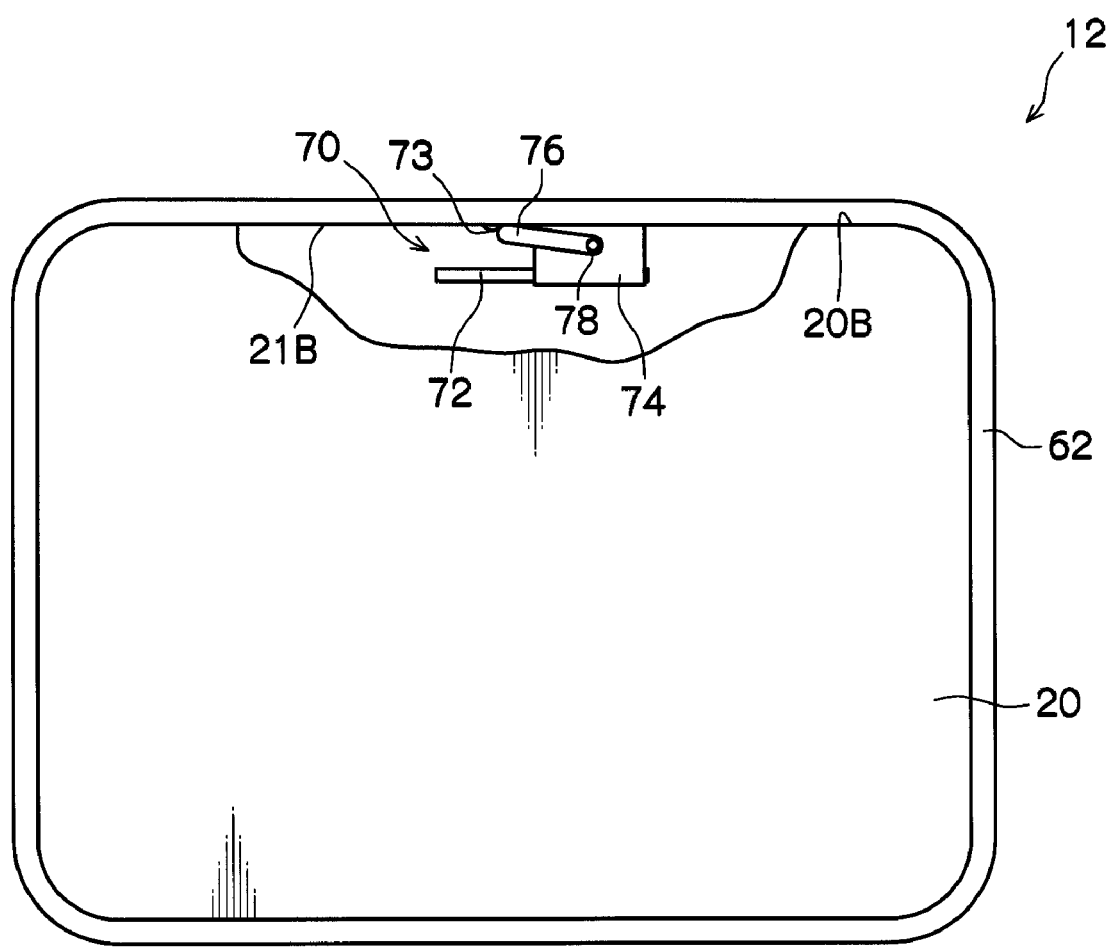
FIG. 10 is a schematic front view showing the opening and closing mechanism according to the exemplary embodiment and showing a state in which the opening is closed.

FIG. 9 is a partial sectional view showing the opening and closing mechanism according to the exemplary embodiment. FIG. 10 is a schematic front view showing the opening and closing mechanism according to the exemplary embodiment and showing a state in which the opening is closed.

The housing 20 of the electronic cassette 12, as shown in FIG. 4, has a shape having four sides 21A, 21B, 21C, and 21D on an outer edge in a plan view, more specifically, parallelogram or four-sides shape (square). More specifically, the housing 20 of the electronic cassette 12 is rectangular in shape. As shown in FIG. 5, the housing 20 of the electronic cassette 12 has round corners (corner portions are chamfered). Note that in FIGS. 2, 3, and 4, the shape of the housing 20 is schematically shown, so, FIGS. 2, 3, and 4 do not show the shape having round corners. The housing 20 of the electronic cassette 12 may have a non-round corners (have angled corners such as right angled corners).

As shown in FIG. 4, a detection area K (TFT active matrix substrate 32) of the radiation ray detector 26 which detects a radiation ray has the same shape as that of the electronic cassette 12. The detection area K has a rectangular shape having long sides arranged along long sides 21B and 21D of the rectangular electronic cassette 12. The detection area K may have a rectangular shape having short sides arranged along the long sides 21B and 21D of the rectangular electronic cassette 12.

Four heat generating portions T which generate heat, as shown in FIG. 4, are arranged at edge portions of the housing 20 along the four sides 21A, 21B, 21C, and 21D to surround the four sides of the detection area K. The heat generating portions T correspond to, for example, the A/D converter of the signal processing unit 48, the control unit 52, the power supply unit 54, a heat generating circuit, which generates heat, of the various circuits, and a heat generating element, which generates heat, of the various elements.

The heat generating portions T may be arranged along at least one side of the four sides 21A, 21B, 21C, and 21D. When the heat generating portions T are arranged along two sides of the four sides 21A, 21B, 21C, and 21D, the heat generating portions T may be arranged along two facing sides (for example, the side 21A and the side 21C). The heat generating portions T may be arranged along two adjacent sides (for example, the side 21A and the side 21B).

In side surfaces 20A, 20B, 20C, and 20D of the housing 20 constituting the four sides 21A, 21B, 21C, and 21D opening portions 60 through which air ventilation of the inside of the housing can be performed with ambient air (air the outside the housing 20) (which can take ambient air into the housing 20) are formed as shown in FIGS. 6 and 7. The side surface 20A corresponds to the side 21A, the side surface 20B corresponds to the side 21B, the side surface 20C corresponds to the side 21C, and the side surface 20D corresponds to the side 21D.

The opening portion 60 is arranged adjacent to the heat generating portion T. Ambient air taken from the opening portion 60 is brought into direct contact with the heat generating portion T.

The opening portions 60 communicate with each other over the circumference (the four side surfaces) of the housing 20, thus are configured by single opening formed at the side surfaces 20A, 20B, 20C, and 20D. The opening portions 60 may be independently formed in the side surfaces 20A, 20B, 20C, and 20D, respectively. Or, at two or three side surfaces of the side surfaces 20A, 20B, 20C, and 20D, the opening portions 60 may communicate with each other. Further, plural opening portions 60 may be formed at the side surface 20B, moreover, plural opening portions 60 also may be formed at the side surfaces 20A, 20C, and 20D respectively.

Further, the number of the opening portions 60 formed at the respective side surfaces 20A, 20B, 20C and 20D may be different, and/or the positions of the opening portions 60 at the respective side surfaces 20A, 20B, 20C and 20D may be different. By this structure, it is possible that suitable number of the opening portions 60 are formed at the side surfaces 20A, 20B, 20C and 20D and/or the opening portions 60 are formed at the suitable positions at the side surfaces 20A, 20B, 20C and 20D in accordance with the respective heat generating portions T.

The opening portions 60 may be arranged to correspond to the heat generating portions T. When the heat generating portion T is arranged along one side of the four sides 21A, 21B, 21C, and 21D, the opening portion 60 may be formed in one side surface in the side surfaces 20A, 20B, 20C, and 20D corresponding to the one side. Therefore, the opening portion 60 may be formed in at least any one of the side surfaces 20A, 20B, 20C, and 20D.

When the opening portions 60 are formed in two side surfaces, the opening portions 60 may be formed in facing side surfaces (for example, the side surface 20A and the side surface 20C), or the opening portions 60 may be formed in adjacent side surfaces (for example, the side surface 20A and the side surface 20B). When the opening portions 60 are formed in the adjacent side surface, one of the opening portions 60 is formed at a position at a right angle to the other opening portion 60.

In the housing 20, as shown in FIGS. 5, 6, and 7, a lid member (a covering member) 62 which covers the opening portions 60 is arranged.

The lid member 62 is formed by an endless annular belt. The single lid member 62 is configured to open and close the opening portions 60 formed in the side surfaces 20A, 20B, 20C, and 20D over the circumference of the housing 20.

The lid member 62 is arranged on the side surfaces 20A, 20B, 20C, and 20D of the housing 20 to cover the side surfaces 20A, 20B, 20C, and 20D and the opening portions 60 from the outer surface side of the housing 20, and is made of an elastic material which absorbs impact acting from the outside of the housing 20. That is, the lid member 62 also functions as a buffering member which absorbs impact acting from the outside of the housing 20. As the elastic material which constitutes the lid member 62, for example, rubber or a resin is used.

The lid member 62 can be moved between a closing position (see FIGS. 5, 6, and 10) where the lid member 62 covers the opening portions 60 from the outside of the housing 20 to close the opening portions 60 and an opening position (see FIGS. 7, 8, and 9) where the lid member 62 moves from the closing position toward the outside of the housing 20 to open the opening portions 60.

On the lid member 62, as shown in FIG. 6, a projecting portion 63 which is inserted into the opening portions 60 at the closing position is formed. With the projecting portion 63, a contact area between the lid member 62 and the housing 20 when the opening portions 60 is closed increases to improve the sealing property of the housing 20.

The electronic cassette 12 has, as shown in FIG. 8, an opening and closing mechanism 70 which opens and closes the lid member 62. The opening and closing mechanism 70 includes a slider 74 slidably arranged on the housing 20, a link member 76 arranged on the slider 74, and a moving mechanism (not shown) which slidably moves the slider 74.

As shown in FIG. 9, the sliders 74, the link members 76, and the moving mechanisms are arranged on both sides of the housing 20 to sandwich the opening portion 60, that is, the opening and closing mechanism 70 includes one pair of sliders 74, one pair of link members 76, and one pair of moving mechanisms. Note that the opening and closing mechanism 70 may include one slider 74, one link member 76, and one moving mechanism.

A distal end portion of the link member 76 is pivotally (rotatably) attached to the lid member 62, and a proximal end portion is pivotally (rotatably) attached to the slider 74.

More specifically, the distal end portion of the link member 76 is fixed to the lid member 62 with an adhesive agent or the like, and is pivoted about a thin portion 73 which is thin as a pivot center. On the other hand, the proximal end portion of the link member 76 is pivotally supported on the slider 74 with a shaft 78 and is pivoted about the shaft 78 as a pivot center.

The slider 74 is attached to a rail 72 arranged on the housing 20, and can be guided by the rail 72 and slidably moved along the side surface 20B of the housing 20. More specifically, the slider 74 can be slidably moved between a facing position (see FIG. 8) where the shaft 78 faces a portion of the lid member 62 to which the distal end portion of the link member 76 is attached and a retreat position (see FIG. 10) where the slider 74 retreats from the facing position by a distance corresponding to a length slightly smaller than that of the link member 76.

When the slider 74 is moved to the facing position by the moving mechanism, as shown in FIG. 8, the longitudinal direction of the link member 76 becomes orthogonal to the side 21B, and the distal end portion of the link member 76 protrudes toward the outside of the housing 20 to push out the lid member 62 toward the outside of the housing 20. In this manner, the lid member 62 moves to the opening position.

On the other hand, when the slider 74 is moved to the retreat position by the moving mechanism, as shown in FIG. 10, the longitudinal direction of the link member 76 becomes to be substantially along (substantially parallel to) the side 21B, and the distal end portion of the link member 76 is accommodated inside the housing 20 and the lid member 62 is drawn from the outside of the housing 20 to the housing 20 side. In this manner, the lid member 62 moves to the closing position.

In this manner, when the slider 74 slidably moves, the link member 76 rises up with respect to the side surface 20B of the housing 20 to move the lid member 62 to the opening position, and the link member 76 tilts with respect to the side surface 20B of the housing 20 to move the lid member 62 to the closing position.

The opening and closing mechanism 70 arranged on the side surface 20B constituting the side 21B is described above. However, the opening and closing mechanism 70 is also arranged on each of the side surfaces 20A, 20C, and 20D, and the opening portions 60 are configured to be independently opened and closed by the lid member 62 on the side surfaces 20A, 20B, 20C, and 20D. The opening and closing mechanism 70 may be arranged at least one of the side surfaces 20A, 20B, 20C, and 20D.

In the above configuration, the moving mechanism which moves the slider 74 is arranged. However, the configuration needs not have the moving mechanism. For example, the slider 74 may be configured to be manually moved.

A fan to circulate ambient air in the housing 20 when the opening portions 60 are opened may be arranged inside the housing 20.

Operation of Electronic Cassette 12 According to Exemplary Embodiment

An operation of the electronic cassette 12 according to the exemplary embodiment will be described below.

In the electronic cassette 12 according to the exemplary embodiment, as shown in FIG. 8, when the slider 74 slidably moves to the facing position by the moving mechanism, the link member 76 rises up with respect to the side surface 20B of the housing 20 to move the lid member 62 to the opening position (see FIG. 7).

In this manner, the opening portion 60 is opened, ambient air flowing into the housing 20 through the opening portion 60 is brought into contact with the heat generating portion T to cool the heat generating portion T. In this manner, deterioration of the constituent components themselves constituting the heat generating portion T, deterioration of peripheral components arranged around the constituent components, deterioration of a photographed image caused by the deterioration in performance of the constituent components themselves and the peripheral components, and the like can be suppressed.

As shown in FIG. 10, when the slider 74 is slidably moved to the retreat position by the moving mechanism, the link member 76 tilts with respect to the side surface 20B of the housing 20 to move the lid member 62 to the closing position. In this manner, the opening portion 60 is closed to set a state in which the lid member 62 covers the side surface 20B of the housing 20 (that is, the lid member 62 covers the side surfaces 20A, 20B, 20C, and 20D) (see FIG. 5).

Since the lid member 62 is made of an elastic material which absorbs impact acting from the outside of the housing, even though the electronic cassette 12 is dropped or even though another object hits against the electronic cassette 12, the lid member 62 absorbs the impact. In this manner, the constituent components may be suppressed from being deteriorated by external impact.

In this manner, according to the electronic cassette 12 of the exemplary embodiment, deterioration of the constituent components caused by external impact and deterioration of the constituent components caused by heat can be suppressed with a small number of components.

According to the electronic cassette 12 of the exemplary embodiment, on the side surfaces 20A, 20B, 20C, and 20D (four sides 21A, 21B, 21C, and 21D) of the housing 20, the opening portions 60 are independently opened. For this reason, only the heat generating portion T to be cooled can be cooled without loss.

The housing 20 and the lid member 62 are easily brought into tight contact with each other because the lid member is made of an elastic material. A contact area between the housing 20 and the lid member 62 is increased by the projecting portion 63 in the closing state. For this reason, sealing property of the housing 20 is improved when the opening portions 60 is closed.

(First Modification of Opening and Closing Mechanism 70)

Figure 11:
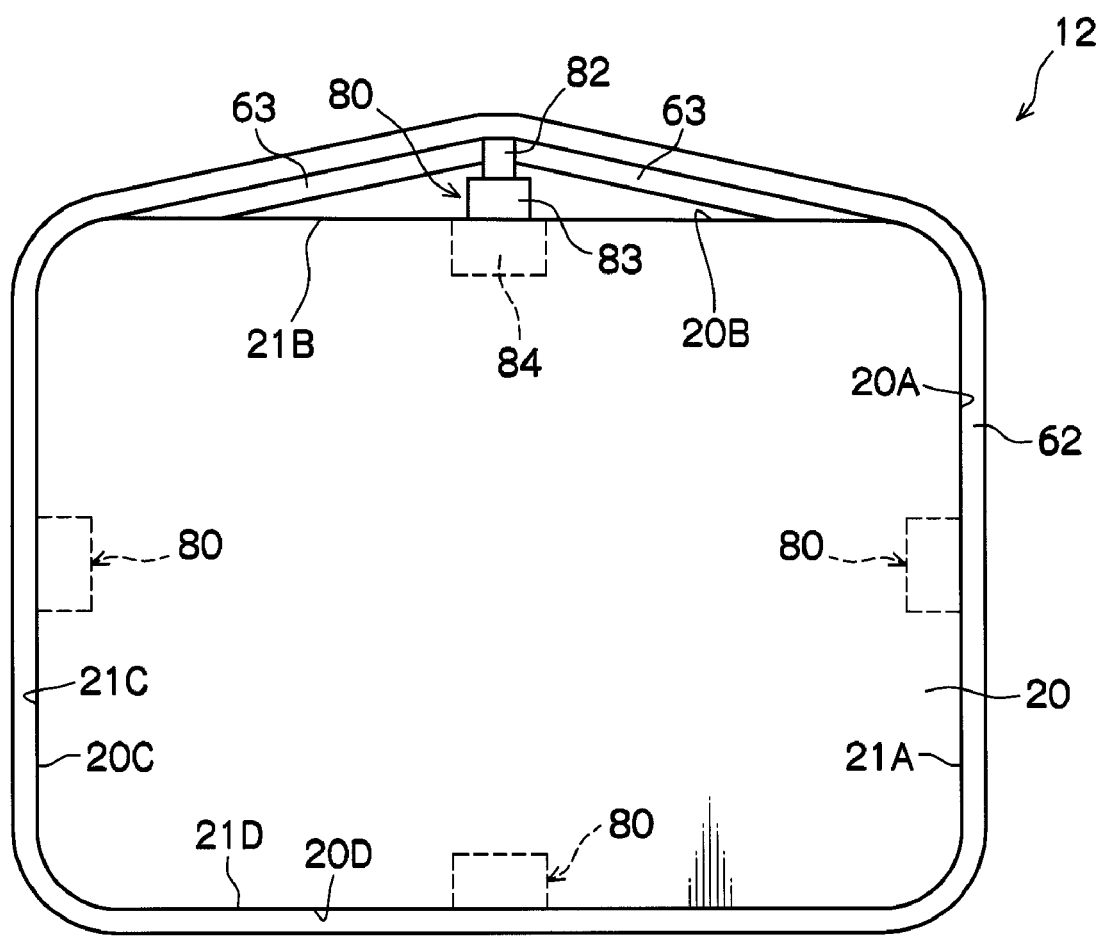
FIG. 11 is a schematic front view showing a configuration of an opening and closing mechanism according to a first modification and showing a state in which the opening is opened.
Figure 12:
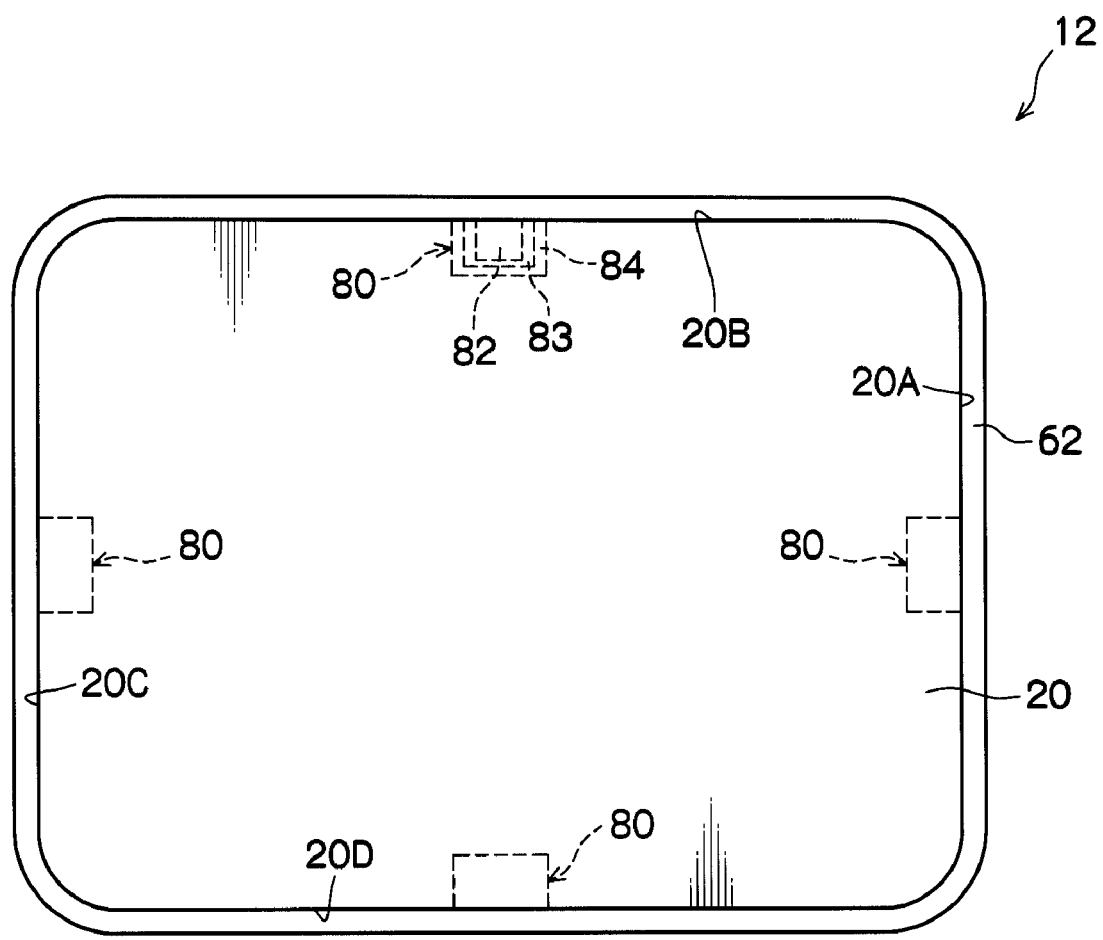
FIG. 12 is a schematic front view showing a configuration of the opening and closing mechanism according to the first modification and showing a state in which the opening is closed.
Figure 13:
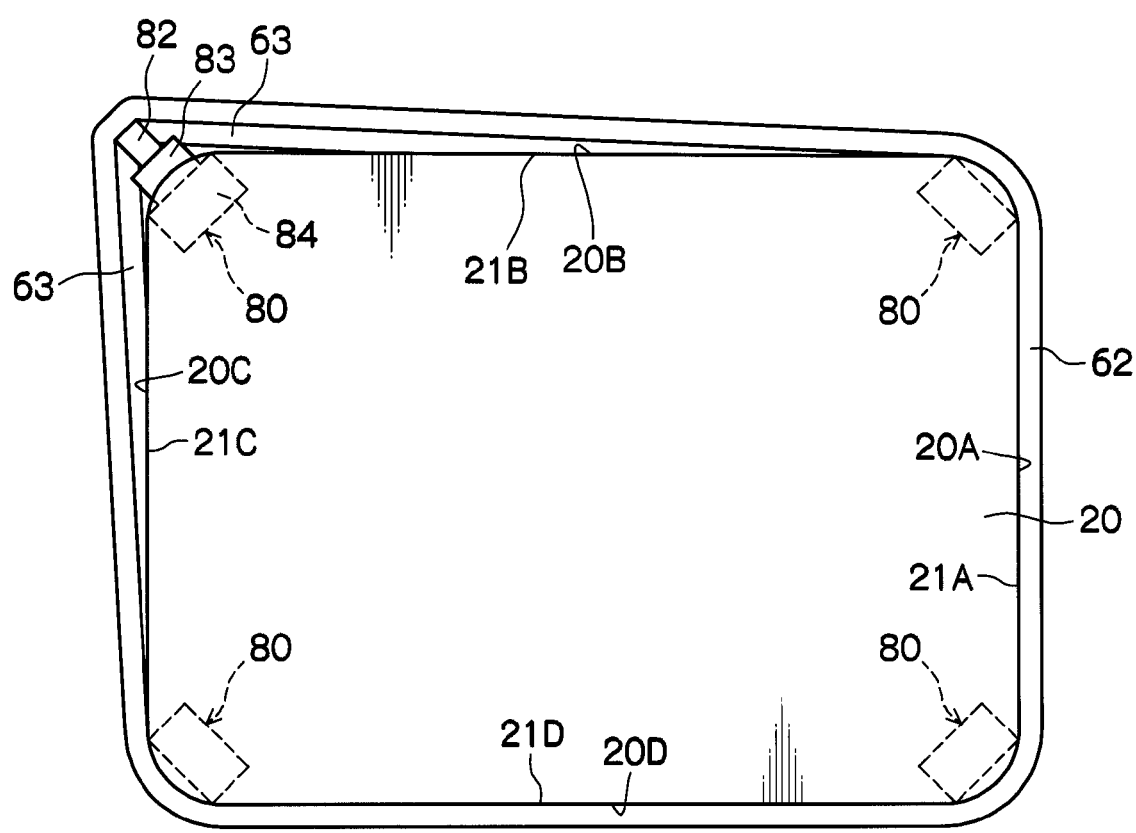
FIG. 13 is a schematic front view showing a configuration in which the opening and closing mechanism according to the first modification is arranged at a corner of the housing.

A first modification of the opening and closing mechanism 70 will be described below. FIG. 11 is a schematic front view showing a configuration of an opening and closing mechanism according to the first modification and showing a state in which the opening portion is opened. FIG. 12 is a schematic front view showing a configuration of the opening and closing mechanism according to the first modification and showing a state in which the opening portion is closed. FIG. 13 is a schematic front view showing a configuration in which the opening and closing mechanism according to the first modification is arranged at a corner of the housing.

An opening and closing mechanism 80 according to the first modification has expandable rods 82 and 83 and a case 84 which houses the rods 82 and 83, arranged on the side surface 20B of the housing 20.

The rods 82 and 83 and the cases 84 are arranged on both sides of the housing 20 to sandwich the opening portion 60, and the opening and closing mechanism 80 is configured by one pair of the rods 82 and 83 and one pair of the cases 84. Note that the opening and closing mechanism 80 is configured by one rod 82, one rod 83, and one case 84.

The distal end portion of the rod 82 is brought into contact with a surface of the lid member 62, and the rods 82 and 83 extend to cause the rod 82 to push the lid member 62, so that the lid member 62 opens the opening portion 60.

When the rods 82 and 83 shrink to be housed in the case 84, the lid member 62 is returned to the closing position by the elastic force of the lid member 62, and the lid member 62 closes the opening portion 60.

As a drive mechanism which drives the rod 82, for example, a solenoid may be used. The opening and closing mechanism 80 is also arranged on each of the side surfaces 20A, 20C, and 20D. The opening portions 60 are configured to be independently opened and closed by the lid member 62 on the side surfaces 20A, 20B, 20C, and 20D. The opening and closing mechanism 70 may be arranged on at least one of the side surfaces 20A, 20B, 20C, and 20D.

The opening and closing mechanism 80 needs not be arranged on each of the side surfaces 20A, 20B, 20C, and 20D of the housing 20. As shown in FIG. 13, for example, the opening and closing mechanism 80 may be configured to be arranged at a corner of the housing 20. The opening and closing mechanisms 80 are arranged at the four corners of the housing 20, respectively.

When the rods 82 and 83 extend to cause the rod 82 to push a portion of the lid member 62 corresponding to the corner portion of the housing 20, the lid member 62 opens the opening portions 60 formed on the side surfaces 20B and 20C. In this configuration, the opening portions 60 formed on the side surfaces 20B and 20C can be opened at once. When the opening portions 60 are arranged at the corners of the housing 20, the dead space of the housing 20 decreases.

(Second Modification of Opening and Closing Mechanism 70)

Figure 14:
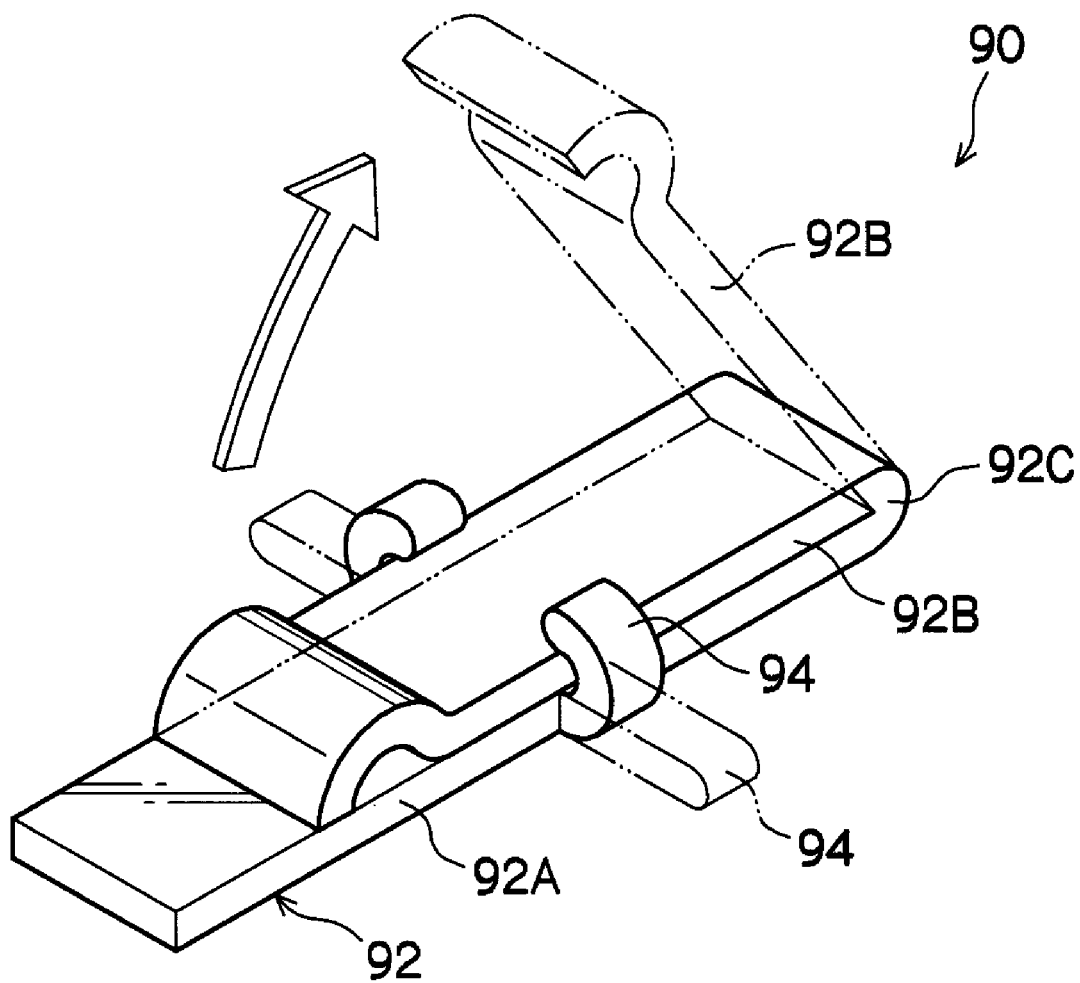
FIG. 14 is a schematic perspective view showing a configuration of an opening and closing mechanism according to a second modification.
Figure 15:
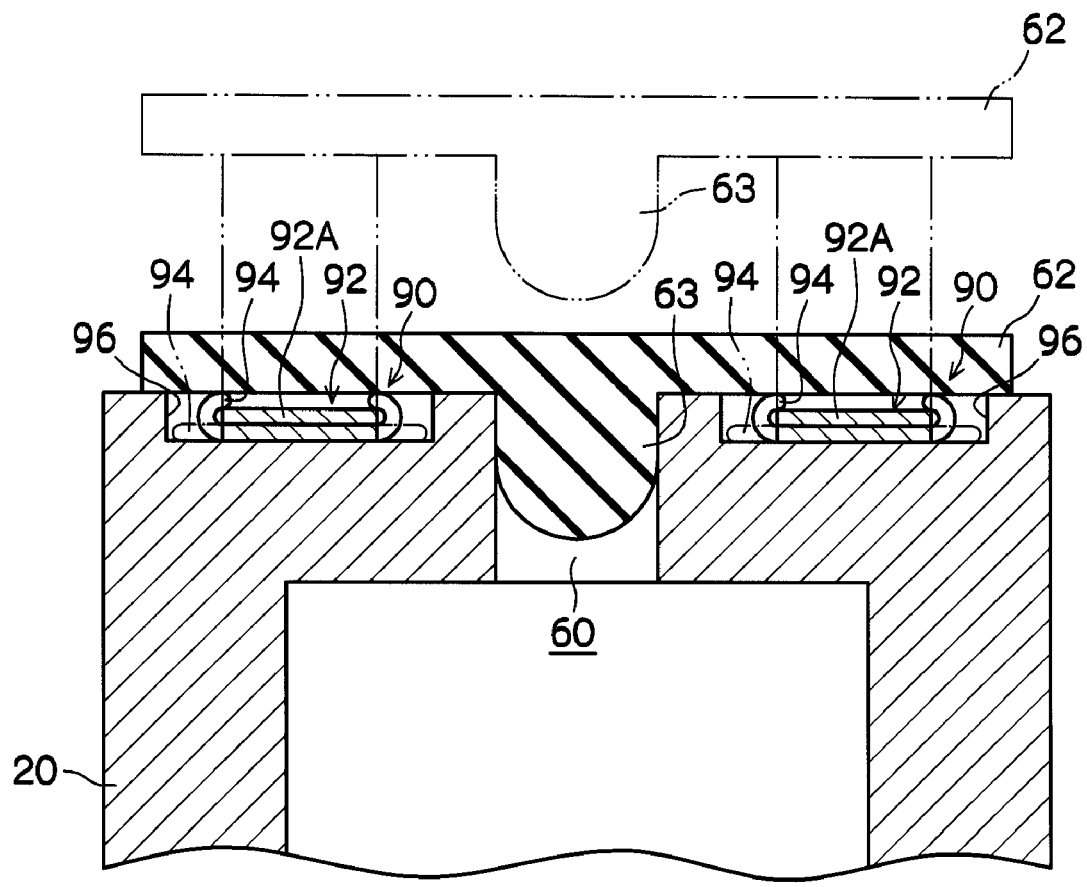
FIG. 15 is a schematic sectional view showing a configuration of the opening and closing mechanism according to the second modification.

A second modification of the opening and closing mechanism 70 will be described below. FIG. 14 is a schematic perspective view showing a configuration of an opening and closing mechanism according to the second modification. FIG. 15 is a schematic sectional view showing a configuration of the opening and closing mechanism according to the second modification.

An opening and closing mechanism 90 according to the second modification includes a biasing member 92 which is biased toward a pushing direction which the lid member 62 is pushed so as to open the lid member 62 with respect to the opening portion, and an engaging member 94 which can be engaged with the biased member 92.

As shown in FIG. 15, the biased members 92 and the engaging members 94 are arranged on both sides of the housing 20 to sandwich the opening portion 60. The opening and closing mechanism 90 is configured by one pair of the biased members 92 and one pair of the engaging members 94. The opening and closing mechanism 90 may be configured by one biasing member 92 and one engaging member 94.

The biasing member 92 is configured by a plate spring. The biasing member 92 includes a bent portion 92C bent at its center, a fixing piece 92A fixed to the housing 20, and a pushing piece 92B connected to the fixing piece 92A at the bent portion 92C to push the lid member 62.

The biased members 92 are housed in recessed housing portions 96 formed in the respective side surfaces 20A, 20B, 20C, and 20D of the housing 20.

The fixing piece 92A is fixed to a bottom surface of the housing portion 96. On the other hand, the pushing piece 92B can be moved between a housing position where the biasing member 92 is folded by the bent portion 92C and the pushing piece 92B is housed in the housing portion 96 and a projecting position where a distal end portion of the pushing piece 92B is separated from the fixing piece 92A to project from the housing portion 96 to the outside of the housing 20. The pushing piece 92B is biased toward the projecting position by elastic force of the biasing member 92.

The distal end portion of the pushing piece 92B is curved in an R (round)-shape, so that an R-shaped contact surface is brought into contact with the lid member 62. The pushing piece 92B pushes the lid member 62 at the projecting position, and the lid member 62 moves to the opening position.

The engaging member 94 is made of a bimetal and configured to be transformed (deformed) in shape by a change due to change of temperature. The engaging member 94 extends (as shown by two-dot chain line in FIG. 14) at a predetermined temperature or more, and an engagement state between the biasing member 92 and the pushing piece 92B is canceled.

The engaging member 94, at a predetermined temperature or less, functions as an engaging hook by bending (curving) so as to be able to engage with the pushing piece 92B of the biasing member 92. In a state in which the engaging member 94 functions as the engaging hook, the pushing piece 92B is pushed toward the fixing piece 92A (the housing 20) side manually or the like so that the pushing piece 92B is engaged with the engaging hook and housed in the housing portion 96.

As the predetermined temperature, for example, a temperature at which deterioration in performance of the constituent components and the peripheral components of the heat generating portion T may be caused is measured in advance at a position where the biasing member 92 is arranged (at the housing portion 96) and the measured temperature may be set as the predetermined temperature.

According to the configuration of the second modification, since the opening portions 60 are automatically opened at the predetermined temperature, additional operation to open the opening portions 60 is not necessary.

(Third Modification of Opening and Closing Mechanism 70)

Figure 16:
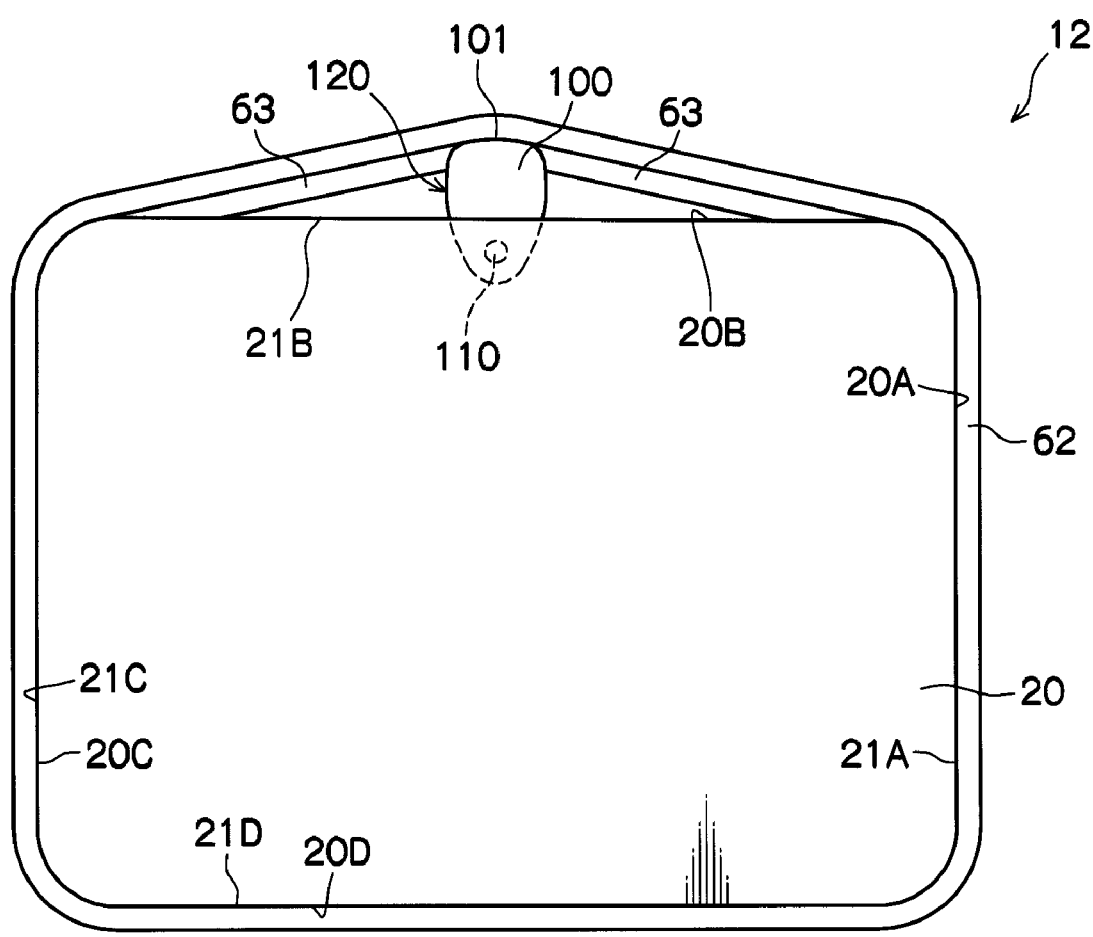
FIG. 16 is a schematic front view showing a configuration of an opening and closing mechanism according to a third modification and showing a state in which the opening is opened.
Figure 17:
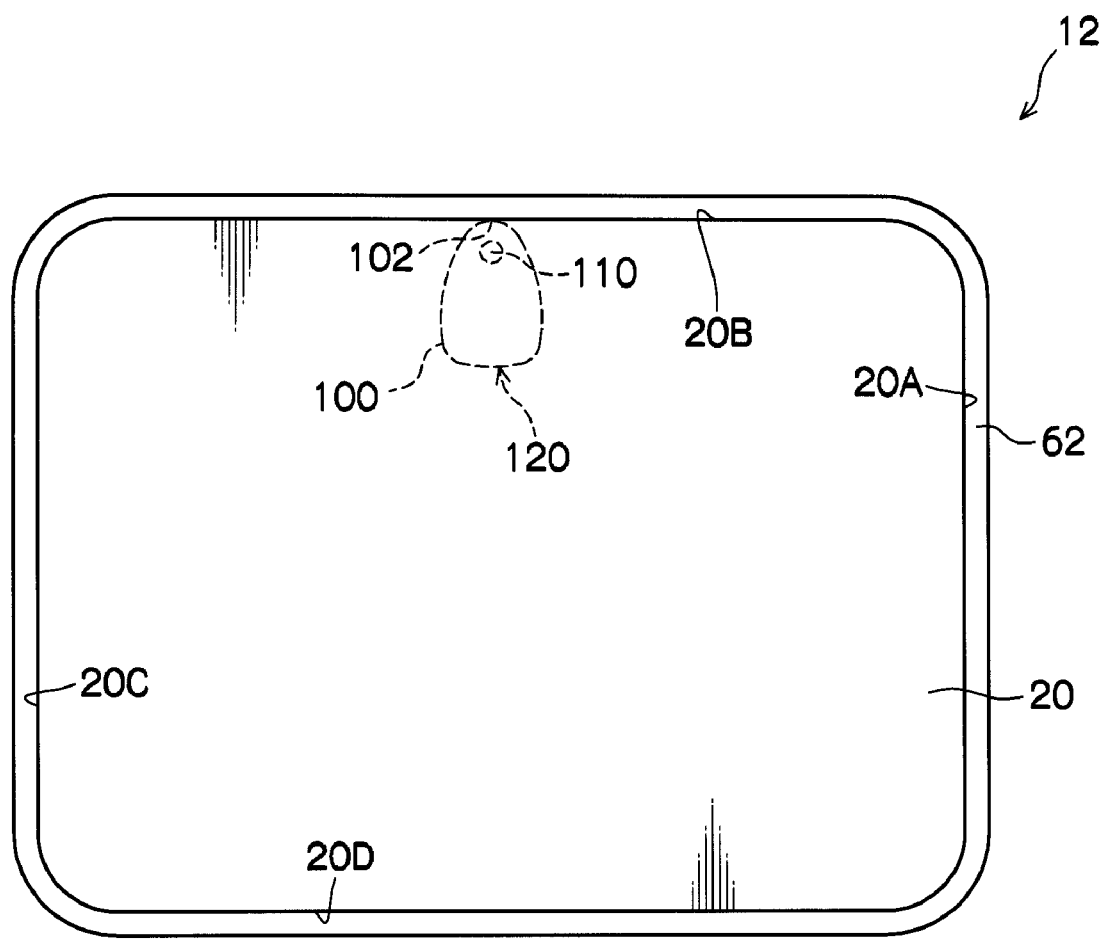
FIG. 17 is a schematic front view showing a configuration of the opening and closing mechanism according to the third modification and showing a state in which the opening is closed.
Figure 18:
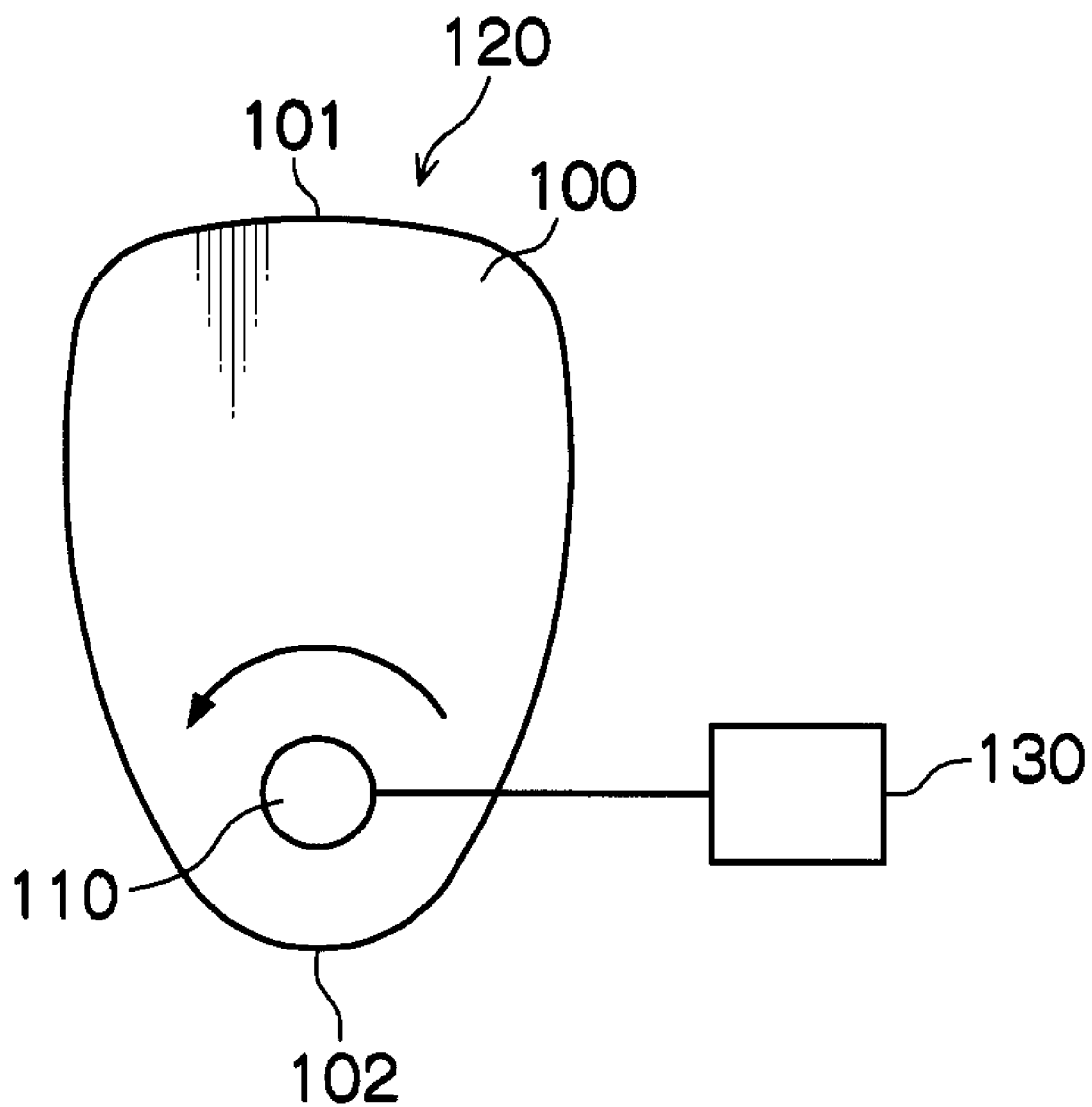
FIG. 18 is a schematic sectional view showing a configuration of the opening and closing mechanism according to the third modification.

A third modification of the opening and closing mechanism 70 will be described below. FIG. 16 is a schematic front view showing a configuration of an opening and closing mechanism 120 according to the third modification and showing a state in which the opening portion is opened. FIG. 17 is a schematic front view showing a configuration of the opening and closing mechanism 120 according to the third modification and showing a state in which the opening portion is closed. FIG. 18 is a schematic sectional view showing a configuration of the opening and closing mechanism 120 according to the third modification.

The opening and closing mechanism 120 according to the third modification has a cam member 100 which is arranged on the side surface 20B of the housing 20, and a motor 130, serving as a rotating driving mechanism, which is connected to the cam member 100 directly or non-directly and rotates the cam member 100 around a rotation axis 110.

The cam members 100 are arranged on both sides of the housing 20 to sandwich the opening portion 60, and the opening and closing mechanism 120 is configured by one pair of the cam members 100. Note that the opening and closing mechanism 120 is configured by one cam member 100.

Note that the opening and closing mechanism 120 according to the third modification is shown only on the side 21B of the housing 20 in FIGS. 16 and 17, however, the opening and closing mechanisms 120 according to the third modification are arranged on the sides 21A, 21B, 21C, 21D of the housing 20 respectively similar to the opening and closing mechanisms 70 according to the first modification as shown in FIGS. 11 and 12. Note that the opening and closing mechanisms 120 may be arranged on one side or any plural sides among the sides 21A, 21B, 21C, 21D of the housing 20.

As shown in FIG. 18, the rotation axis 110 is arranged in an eccentric manner at the cam member 100. The cam member 100 includes a far portion 101 which is located at the farthest position from the rotation axis 110 and a near portion 102 which is located at the nearest position from the rotation axis 110.

The position of the rotation axis 110 is set such that, when the cam member 100 is rotated by the driving force of the motor 130 and the far portion 101 of the cam member 100 faces to a portion of the surface of the lid member 62 while contacting with the portion of the surface of the lid member 62, the far portion 101 of the cam member 100 pushes the lid member 62 toward the outside of the housing 20, as shown in FIG. 16, and when the cam member 100 is rotated and the near portion 102 of the cam member 100 faces to the portion of the surface of the lid member 62, the near portion 102 of the cam member 100 does not push the lid member 62 so the lid member 62 is returned to the closing position, as shown in FIG. 17.

Note that, when the lid member 62 is returned to the closing position (when the near portion 102 faces the portion of the surface of the lid member 62), the near portion 102 of the cam member 100 may be located at a position which is apart from the surface of the lid member 62, or may be located at a position where the near portion 102 merely contacts with the portion of the surface of the lid member 62 (the near portion 102 does not push the lid member 62).

When the cam member 100 is rotated by the motor 130, while the outer peripheral surface of the cam member 100 is brought into contact with the surface of the lid member 62, the cam member 100 gradually pushes the lid member 62 outwardly, so the lid member 62 gradually opens the opening portion 60, and the opening state becomes in the maximum state when the far portion 101 faces the portion of the surface of the lid member 62 as shown in FIG. 16.

When the cam member 100 is further rotated, while the outer peripheral surface of the cam member 100 is brought into contact with the surface of the lid member 62, the lid member 62 gradually closes the opening portion 60, and when the near portion 102 faces the portion of the surface of the lid member 62 as shown in FIG. 17, the lid member 62 is returned to the closing position by the elastic force of the lid member 62, and the lid member 62 closes the opening portion 60.

Note that a cam member whose structure is different from that of the cam member 100 in the drawings can be used in the opening and closing mechanisms 120. The opening and closing mechanism 120 is also arranged on each of the side surfaces 20A, 20C, and 20D as mentioned above, so the opening portions 60 are configured to be independently opened and closed by the lid member 62 on the side surfaces 20A, 20B, 20C, and 20D.

Note that the opening and closing mechanism 120 needs not be arranged on each of the side surfaces 20A, 20B, 20C, and 20D of the housing 20. Similar to the first modification as shown in FIG. 13, for example, the opening and closing mechanism 120 may be configured to be arranged at the corner or corners of the housing 20.

The invention is not limited to the above exemplary embodiment. Various modifications, changes, and improvements of the invention may be effected.

What is claimed is:

1. A radiation photographing apparatus comprising:
   a housing in which an opening portion for allowing ventilation of the inside of the housing with ambient air is formed at a side surface of the housing;
   a covering member provided at the side surface of the housing, that is made of an elastic material which absorbs an impact from outside the housing, and covers the opening portion; and
   an opening and closing mechanism that opens and closes the covering member with respect to the opening portion.

2. The radiation photographing apparatus of claim 1, wherein
   opening portions are formed in a plurality of side surfaces of the housing respectively, and
   opening and closing mechanisms are provided at the respective side surfaces, and independently open and close the covering member at the respective side surfaces.

3. The radiation photographing apparatus of claim 2, wherein each of the opening and closing mechanisms includes:
   a slider that is arranged to be slidably movable on the housing; and
   a link member whose distal end portion is rotatably attached to the covering member and whose proximal end portion is rotatably attached to the slider, and that opens the covering member by the distal end portion pushing the covering member toward the outside of the housing due to the slider moving to a facing position that faces a position of the covering member at which the distal end portion is attached.

4. The radiation photographing apparatus of claim 2, wherein each of the opening and closing mechanisms includes an extendable rod that opens the covering member by extending to push the covering member.

5. The radiation photographing apparatus of claim 2, wherein each of the opening and closing mechanisms includes:
   a biasing member that is biased toward a pushing position where the biasing member opens the covering member by pushing the covering member; and
   an engaging member that is engaged with the biasing member, and that is deformed at a predetermined temperature so as to release an engaging state with the biasing member to allow the biasing member to move to the pushing position.

6. The radiation photographing apparatus of claim 5, wherein the engaging member is made of bimetal that extends at the predetermined temperature.

7. The radiation photographing apparatus of claim 2, wherein each of the opening and closing mechanisms includes:
   a cam member that is arranged to be rotatable on the housing; and
   a rotating driving section, connected to the cam member, that rotates the cam member,
   wherein the cam member includes a far portion which is located at the farthest position from a rotation axis of the cam member and a near portion which is located at the nearest position from the rotation axis, and
   when the cam member is rotated by the rotating driving section, and the far portion moves to a position where the far portion faces a portion of the covering member, the covering member opens the opening portion by the far portion pushing the covering member toward the outside the housing, and when the cam member is rotated by the rotating driving section, and the near portion moves to a position where the near portion faces the portion of the covering member, the covering member closes the opening portion.

8. The radiation photographing apparatus of claim 1, wherein the opening and closing mechanism includes:
   a slider that is arranged to be slidably movable on the housing; and
   a link member whose distal end portion is rotatably attached to the covering member and whose proximal end portion is rotatably attached to the slider, and that opens the covering member by the distal end portion pushing the covering member toward the outside of the housing due to the slider moving to a facing position that faces a position of the covering member at which the distal end portion is attached.

9. The radiation photographing apparatus of claim 1, wherein the opening and closing mechanism includes an extendable rod that opens the covering member by extending to push the covering member.

10. The radiation photographing apparatus of claim 9, wherein the opening and closing mechanism is provided at a corner portion of the housing.

11. The radiation photographing apparatus of claim 9, wherein the opening and closing mechanism is provided at the side surface.

12. The radiation photographing apparatus of claim 1, wherein the opening and closing mechanism includes:
   a biasing member that is biased toward a pushing position where the biasing member opens the covering member by pushing the covering member; and
   an engaging member that is engaged with the biasing member, and that is deformed at a predetermined temperature so as to release an engaging state with the biasing member to allow the biasing member to move to the pushing position.

13. The radiation photographing apparatus of claim 12, wherein the engaging member is made of bimetal that extends at the predetermined temperature.

14. The radiation photographing apparatus of claim 1, wherein
   a plurality of opening portions are formed in the side surface of the housing.

15. The radiation photographing apparatus of claim 1, wherein the opening and closing mechanism includes:
   a cam member that is arranged to be rotatable on the housing; and
   a rotating driving section, connected to the cam member, that rotates the cam member,
   wherein the cam member includes a far portion which is located at the farthest position from a rotation axis of the cam member and a near portion which is located at the nearest position from the rotation axis, and
   when the cam member is rotated by the rotating driving section, and the far portion moves to a position where the far portion faces a portion of the covering member, the covering member opens the opening portion by the far portion pushing the covering member toward the outside the housing, and when the cam member is rotated by the rotating driving section, and the near portion moves to a position where the near portion faces the portion of the covering member, the covering member closes the opening portion.

16. A radiation photographing apparatus comprising:
   a housing in which an opening for allowing ventilation of the inside of the housing with ambient air is formed at a side surface of the housing;
   a covering member provided at the side surface of the housing, that is made of an elastic material which absorbs an impact from outside the housing, and covers the opening portion; and
   an opening and closing mechanism that opens and closes the covering member with respect to the opening portion,
   wherein the opening and closing mechanism opens the covering member with respect to the opening portion by pushing to elastically deform the covering member toward the outside of the housing.

17. The radiation photographing apparatus of claim 16, wherein
   opening portions are formed in a plurality of side surfaces of the housing respectively, and
   opening and closing mechanisms are provided at the respective side surfaces, and independently open and close the covering member at the respective side surfaces.

18. The radiation photographing apparatus of claim 16, wherein the opening and closing mechanism includes:
   a slider that is arranged to be slidably movable on the housing; and
   a link member whose distal end portion is rotatably attached to the covering member and whose proximal end portion is rotatably attached to the slider, and that opens the covering member by the distal end portion pushing the covering member toward the outside of the housing due to the slider moving to a facing position that faces a position of the covering member at which the distal end portion is attached.

19. The radiation photographing apparatus of claim 16, wherein the opening and closing mechanism includes an extendable rod that opens the covering member by extending to push the covering member.

20. The radiation photographing apparatus of claim 16, wherein
   the opening and closing mechanism includes:
   a biasing member that is biased toward a pushing position where the biasing member opens the covering member by pushing the covering member; and
   an engaging member that is engaged with the biasing member, and that is deformed at a predetermined temperature so as to cancel an engaging state with the biasing member to allow the biasing member to move to the pushing position.

* * * * *